United States Patent [19]

Nakayama et al.

[11] 4,307,034

[45] Dec. 22, 1981

[54] INERT ORGANIC SOLVENT DISPERSION OF ALKALI HYDROXIDE AND REACTION USING THE SAME

[75] Inventors: Yoshiki Nakayama, Shimizu; Taro Izawa, Shizuoka; Yasushi Higuchi, Shizuoka; Yutaka Ohishi, Shizuoka; Chihiro Yazawa, Yokohama, all of Japan

[73] Assignee: Ihara Chemical Industry Co., Ltd., Tokyo, Japan

[21] Appl. No.: 75,314

[22] Filed: Sep. 13, 1979

[30] Foreign Application Priority Data

Sep. 26, 1978 [JP] Japan ............................. 53/118501
Oct. 30, 1978 [JP] Japan ............................. 53/133379
Oct. 30, 1978 [JP] Japan ............................. 53/133380

[51] Int. Cl.$^3$ .................. C07C 121/66; C07C 53/34; C07C 55/08; C07C 121/22
[52] U.S. Cl. ................... 260/465 G; 252/309; 260/465 R; 260/465 D; 260/465 F; 260/465 H; 260/465 K; 260/465.4; 260/465.8 R; 560/51; 560/82; 560/178; 560/190; 562/405; 562/459; 562/489; 562/495; 562/496; 562/590; 562/595; 568/316; 568/376; 568/393; 568/433; 568/458; 568/459
[58] Field of Search .......... 260/465 R, 465 G, 465 H, 260/465.4, 465 F, 465 D, 465 K, 465.8 R; 560/51, 82, 190, 178; 562/489, 495, 496, 590, 595, 405, 459; 568/316, 376, 393, 458, 459, 433

[56] References Cited

U.S. PATENT DOCUMENTS 3,755,412  8/1973  Taranko et al. ................ 260/465 R
4,012,428  3/1977  Ohno et al. ..................... 260/465 G
4,062,968  12/1977 Fujimoto et al. ............... 424/304 X

*Primary Examiner*—Dolph H. Torrence
*Attorney, Agent, or Firm*—Oblon, Fisher, Spivak, McClelland & Maier

[57] ABSTRACT

An inert organic solvent dispersion of alkali hydroxide is prepared by mixing an alkali hydroxide, an inert organic solvent and a stabilizer and heating and stirring at the temperature for forming the pasty alkali hydroxide and cooling the dispersion. The dispersion of alkali hydroxide is used in a reaction of an active methylene compound with an organoalkyl halide such as a reaction of a halophenylacetonitrile with an isopropyl halide to obtain α-isopropyl halophenylacetonitrile.

8 Claims, No Drawings

INERT ORGANIC SOLVENT DISPERSION OF ALKALI HYDROXIDE AND REACTION USING THE SAME

BACKGROUND OF THE INVENTION

1. Field of the Invention

The present invention relates to a process for preparing an inert organic solvent dispersion of an alkali hydroxide. More particularly, it relates to a process for preparing an inert organic solvent dispersion of fine alkali hydroxide particles having a diameter of order of $m\mu$ to $\mu$ such as 100 $m\mu$ to 500$\mu$.

The present invention also relates to a reaction using the same. More particularly, it relates to the reaction of an active methylene compound with an organoalkyl halide to produce methylene organoalkylated compounds useful as intermediates of agricultural chemicals and medicines. More particularly, it relates to a process for producing methylene organoalkylated compounds by reacting an active methylene compound with an organoalkyl halide in the presence of an alkali hydroxide.

2. Description of the Prior Arts

Heretofore, it has been difficult to obtain fine alkali hydroxide particles because of strong hygroscopic property of the alkali hydroxide.

On the other hand, an aqueous solution of a base such as alkali hydroxides or carbonates has been used for reactions of a halogenated compound with a compound having an activated hydrogen atom, such as a condensation reaction.

When an aqueous solution of a base is used for the condensation reaction such as dehydrohalogenation, the product may be decomposed because of the aqueous solution of a base.

In order to overcome the problem, it has been considered to use a solid base such as alkali hydroxides or carbonates. However, alkali hydroxides are hygroscopic and are insoluble in an inert organic solvents.

However, these conventional processes have various disadvantages and are not satisfactory process as the industrial process.

In the process (1), the condensing agent is remarkably reactive with water and accordingly, the activity of the condensing agent is decreased by the contamination of water to decrease the yield of the object compound. The explosive reaction may be caused by reacting the condensing agent with water to cause firing. Thus, the storage and maintenance of the starting materials and the operation for the reaction are quite difficult to be disadvantageous.

In the process (2), the expensive and water soluble aprotic polar solvent such as dimethylsulfoxide is used as the solvent. This is not easily recovered. Thus, it is disadvantageous from the economical viewpoint.

In the process (3), the expensive and water soluble quaternary ammonium salt is used as the catalyst. The discharge of the quaternary ammonium salt in a drainage can not be prevented whereby the nitrogen content in river, sea or lake is increased to cause the environmental pollution. Thus, it is disadvantageous from the economical viewpoint.

The inventors have studied to overcome these disadvantages of the conventional processes.

It has been well-known to produce methylene organoalkylated compounds by reacting an active methylene compound with an organoalkyl halide in the presence of an alkali hydroxide.

(1) The reaction is carried out in the presence of an alkali hydroxide (Organic Reactions Vo. 9, page 107).

(2) The reaction is carried out in a reaction medium of an aprotic polar solvent such as dimethylsulfoxide (J. Org. Chem. Vol. 34, pages 226, 1969).

(3) The reaction is carried out in the presence of a catalyst of a quaternary ammonium salt (Acta. Chem. Scand. Vol. 23, page 2204, 1969; Tetrahedron Lett. Vol. 15, 1273, 1973; Tetrahedron Vol. 32, page 2235, 1976).

One of the important examples of the reaction of the active methylene compound with an organoalkyl halide is the production of $\alpha$-isopropyl halophenylacetonitrile.

(1) The reaction is carried out in the presence of a condensing agent such as alkali metals, alkali metal alcoholates, alkali metal halides or alkali metal amides (Japanese Unexamined Patent Publication No. 5350/1975).

(2) The reaction is carried out in the presence of a condensing agent of an alkali hydroxide in a medium of an aprotic polar solvent such as dimethylsulfoxide and dimethylformamide (Japanese Unexamined Patent Publication No. 154217/1975).

(3) The reaction is carried out in the presence of a condensing agent of an alkali hydroxide and a catalyst of a quaternary ammonium salt (Japanese Unexamined patent Publication No. 63145/1976).

SUMMARY OF THE INVENTION

It is an object of the present invention to provide a process for preparing an inert organic solvent dispersion of fine alkali hydroxide particles having a diameter of 100 $m\mu$ to 500$\mu$.

It is another object of the present invention to provide a process for preparing an inert organic solvent dispersion of alkali hydroxide which is used for a condensation reaction of a halogenated compound with a compound having an active hydrogen.

The foregoing and other objects of the present invention have been attained by mixing a solid alkali hydroxide, and an inert organic solvent and heating and stirring the mixture and cooling the mixture in the dispersed form.

The mixture is heated so as to form a pasty alkali hydroxide in the inert organic solvent.

The stirring is carried out so as to form fine particles of the alkali hydroxide. The stirring is continued after starting the cooling. It is preferable to add a stabilizer.

The reaction of an active methylene compound with an organoalkyl halide is carried out by using the inert organic solvent dispersion of fine alkali hydroxide whereby a methylene organoalkylated compound having high purity can be obtained in high yield without using an expensive aprotic polar solvent such as dimethyl sulfoxide and without a recovery of a catalyst such as a quarternary ammonium salts.

DETAILED DESCRIPTION OF THE PREFERRED EMBODIMENTS

The dispersion of the alkali hydroxide is prepared by using the inert organic solvent which is suitable for swelling the alkali hydroxide to form the pasty alkali hydroxide in the solvent at the elevated temperature. It is preferable to use the inert organic solvent which can be used in the atmospheric pressure. The detail of the operation for the preparation of the dispersion will be described.

Suitable inert organic solvents include aromatic hydrocarbons such as benzene, toluene and xylene; halogenated aromatic hydrocarbons such as chlorobenzene and chlorotoluene; halogenated aliphatic hydrocarbons such as chloroform and carbon tetrachloride and other solvents which have boiling point of higher than 100° C. preferably higher than 120° C.

The stirring operation is easily carried out and the hygroscopic property of the alkali hydroxide can be prevented and the formation of fine particles of the alkali hydroxide can be promoted by stirring and solid alkali hydroxide in said inert organic solvent.

The amount of the inert organic solvent should be enough to stir the mixture and is preferably more than 2 times of the alkali hydroxide.

The stabilizers can be the compounds having the formula

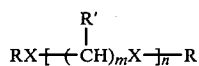

wherein R and R' are respectively hydrogen atom or $C_1$-$C_4$ alkyl group and X represents oxygen or sulfur atom; m and n are respectively 1 or more than 1; and polyoxyethylene type nonionic surfactants, fatty acid sorbitan esters, fatty acid glycerol monoesters and fatty acid sugar esters, quaternary ammonium salts, fatty amines and perfluoroalkyl surfactants.

Suitable stabilizers include; monoalkyl glycol ethers e.g. monomethyl, monoethyl, monopropyl or monostearyl glycol ethers; dialkyl glycol ethers e.g. dimethyl, diethyl, dipropyl or dibutyl glycol ethers; glycols such as polymethyleneglycol, ethyleneglycol, diethyleneglycol, triethyleneglycol, tetraethyleneglycol, hexaethyleneglycol, pentaethyleneglycol, isopropyleneglycol, polyethyleneglycol, propyleneglycol, dipropyleneglycol, tripropyleneglycol, trapropyleneglycol, polypropyleneglycol and 1,4-butanediols; polyvinyl ethers; monoalkylsulfides e.g. monomethyl, monoethyl, monopropyl and monobutyl sulfides; dialkylsulfides e.g. dimethyl, diethyl, dipropyl and dibutyl sulfides; thioglycols such as ethylenethioglycol, diethylenethioglycol, triethylenethioglycol, tetraethylenethioglycol, polyethylenethioglycol and polymethylenethioglycol; polyoxyethlene type nonionic surfactants; fatty acid sorbitan esters; fatty acid glycerol monoesters; sugar esters; fatty amines; quaternary ammonium salts; and perfluoroalkyl surfactants.

Suitable polyoxyethylene type nonionic surfactants include polyoxyethylenealkyl esters such as polyoxyethylenedodecyl ether, polyoxyethyleneoctadecyl ether and polyoxyethylenenonyl ether; polyoxyethylenealkylaryl ethers such as polyoxyethylenenonylphenyl ehter, polyoxyethylene fatty acid esters such as polyoxyethylenestearate and polyoxyethylenedistearate; polyoxyethylenesorbitane fatty acid esters such as polyoxyethylenesorbitanemonolaurate, -monoparamitate, -monostearate, -monooleate, -tristearate, and -trioleate; polyoxyethylenealkylamine such as polyoxyethylene dodecylamine.

Suitable fatty acid sorbitane esters include sorbitanemonolaurate, -monoparmitate, -monostearate, -monooleate, -tristearate, -trioleate and -sesquioleate.

Suitable fatty acid esters include glycerol monostearate and glycerol monooleate.

Suitable fatty amines include oleyl dimethylamine, coconut oil dimethylamine and lauryl dimethylamine.

Suitable quaternary ammonium salts include lauryltrimethylammonium chloride and stearyltrimethylammonium chloride and alkylbenzyldimethylammonium chloride.

Suitable perfluoroalkyl surfactants include perfluoroalkylsulfonate, such as perfluorooctylsulfonate; perfluoroalkylsulfonylamine derivatives such as perfluorooctylsulfonylamine hydrohalide, perfluorooctylsulfonylpropylamine ethyleneoxide adduct and -sulfonylbenzylamine ethyleneoxide adduct.

The amount of the stabilizer is usually more than 0.0001 wt. % preferably more than 0.001 wt. % especially more than 0.01 wt. % to the alkali hydroxide. The stabilizer can be a mixture of said compounds. The stabilizer is to prevent the coagulation of the dispersed alkali hydroxide in the inert organic solvent by adsorbing it on the surface of the fine alkali hydroxide particles whereby the formation of fine particles of the alkali hydroxide is improved and to prevent a deposition of the alkali hydroxide on the inner wall of the reactor.

The stabilizer should have hydrophilic property so as to be adsorbed on the surface of the alkali hydroxide in the inert organic solvent which is not hydrophilic solvent.

The heating and stirring of the mixture of the alkali hydroxide and the inert organic solvent are preferably carried out near the boiling point of the solvent. When the inert organic solvent having low boiling point is used, it is preferable to carry out under higher pressure. It is preferable to carry out the stirring at higher than 120° C. in the atmospheric pressure. The temperature can be decreased under higher pressure.

The stirring should be enough to disperse the alkali hydroxide in the inert organic solvent, with or without the stabilizer. The stirring method is not critical. Suitable stirrer, homomixer, ultrasonic disperser or jet disperser can be used to apply share enough to disperse the alkali hydroxide.

When a stirrer is used, the stirrer is preferably rotated at greater than 500 r.p.m. preferably greater than 1,000 r.p.m. It is possible to stir at greater than 3,000 r.p.m. such as 10,000 r.p.m. as used in the homogenizer.

The ultrasonication or the jet dispersion is preferably applied together with the mechanical stirring so as to share the alkali hydroxide.

The melting point of the alkali hydroxide is usually high as 360.4° C. of KOH and 328° C. of NaOH. In the operation, the alkali hydroxide is dispersed at lower than the melting point of the alkali hydroxide, however the alkali hydroxide is preferably pasty in the inert organic solvent at the elevated temperature.

The dispersion of fine alkali hydroxide particles having orders of $m\mu$ to $\mu$ such as 100 $m\mu$ to 500$\mu$ can be obtained by the process of the present invention. It is possible to separate the organic solvent from the dispersion by a filtration or a distillation to obtain the fine alkali hydroxide powder which can be dispersed in a desired solvent. It is preferable to use an inert organic solvent which is used for the reaction of a halogenated compound with a compound having active hydrogen atom. The dispersion of the fine alkali hydroxide in said solvent can be used for the reaction without the separation or the exchange of the solvent.

In accordance with the process of the present invention, the dispersion of fine alkali hydroxide or fine alkali hydroxide powder can be easily obtained, and moreover the adhesion of the alkali hydroxide on the inner wall of the reactor can be prevented. These are remarkably advantageous. The size of the resulting particles of the alkali hydroxides is controlled by the stirring method to give 100 mμ to 500μ.

The dispersion of fine alkali hydroxide is remarkably effective for condensation reactions such as alkylations especially alkylation of active methylene group.

The inert organic solvent dispersion of an alkali hydroxide is the novel important reactant for the reaction of an active methylene compound with an organoalkyl halide.

The organoalkyl halide is added to the inert organic solvent dispersion of an alkyl hydroxide and the active methylene compound is added to it so as to react them.

The reaction of the active methylene compound with the organoalkyl halide is carried out in a dispersion of fine alkali hydroxide particles having diameter of less than several hundred microns as the condensing agent.

A dispersion of fine potassium hydroxide in an inert organic solvent is preferably used. The reaction is smoothly performed without a special condensing agent nor a special solvent nor a special catalyst to obtain α-isopropyl halophenylacetonitrile having high purity in high yield.

In the process of the present invention, a dispersion of fine alkali hydroxide is admixed with the organoalkyl halide and the active methylene compound is added to react them.

The reaction temperature is in a range of 0° to 150° C. preferably 20° to 60° C. The reaction is carried out under the atmospheric pressure or the elevated pressure. The reaction time is preferably 0.5 to 1 hour and is not critical.

The reaction solvent is not critical and is preferably an inert organic solvent such as benzene, toluene, xylene, chlorobenzene and dichlorotoluene.

The dispersion of fine alkali hydroxide can be obtained by mixing an alkali hydroxide such as potassium hydroxide and a stabilizer and an inert organic solvent such as benzene, toluene, xylene, chlorobenzene and dichlorotoluene and heating and stirring the mixture to disperse the alkali hydroxide and cooling the dispersion. The stabilizer can be the compound having the formula

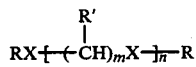

wherein R and R' are respectively hydrogen atom or $C_1$-$C_4$ alkyl group; X represents oxygen or sulfur atom; m and n are respectively 1 or more than 1; and polyoxyethylene type nonionic surfactants, fatty acid sorbitan esters, fatty acid glycerol monoesters, fatty acid sugar esters, quaternary ammonium salts, fatty amines; perfluoroalkyl surfactsnts, powdery titanium oxides and powdery zirconium oxides.

The amount of the fine alkali hydroxide is at a molar ratio of 1 to 10 preferably 3 to 6 based on the active methylene compound.

The active methylene compounds can be various compounds having active methylene group.

Suitable active methylene compounds include malonic nitrile, malonic acid, diethyl malonate, cyanoacetic acid, methyl cyanoacetate, acetylacetic acid, methyl acetylacetate, acetylacetone, phenylacetonitrile, 4-ethylphenylacetonitrile, 3,4-dimethylphenylacetonitrile, 3-trifluoromethylphenylacetonitrile, phenylacetic acid, 4-chlorophenyl acetic acid, 2-bromophenyl acetic acid, 4-ethylphenyl acetic acid, phenylthioacetonitrile, α-methylphenylacetonitrile, α-methoxyphenylacetonitrile, β-cyanophenylpropionitrile, diphenylacetonitrile, propionaldehyde, cyclohexanone, and 2-methylcyclohexanone and their derivatives.

Suitable organoalkyl halides include alkyl halides such as methyl, ethy, propyl, butyl, pentyl, hexyl, octyl and nonyl halides; dihalides thereof such as dihaloethanes, dihalopropanes, dihalobutanes; trihalides thereof; aralkyl halides such as benzyl halides; vinyl halides; alkyl vinyl halides; haloacetyl compounds such as haloacetonitriles and haloacetates.

The organoalkyl compound is used at molar ratio of 1 to 5 based on the active methylene compound.

The example of the production of α-isopropyl halophenylacetonitrile will be further illustrated.

As one typical example, the reaction of halophenylacetonitrile with isopropyl halide to produce α-isopropyl halopheylacetonitrile will be illustrated.

The dispersion of the alkali hydroxide in an inert organic solvent can be used at a molar ratio of 1 to 10 preferably 3 to 6 based on the halophenylacetonitrile.

Suitable halophenylacetonitriles include 2-chlorophenylacetonitrile, 3-chlorophenylacetonitrile, 4-chlorophenylacetonitrile, 4-bromophenylacetonitrile, 3-fluorophenylacetonitrile and 4-fluorophenylacetonitrile.

Suitable isopropyl halides include isopropyl bromide and isopropyl chloride.

The isopropyl halide is used at a molar ratio of 1 to 5 based on the halophenylacetonitrile.

The alkali hydroxides include sodium hydroxide and potassium hydroxide.

The process of the present invention is remarkably effective and has the following advantages in comparison with the conventional process and is remarkably advantageous as an industrial process.

Firstly, a dimer of halophenylacetonitrile having the formula

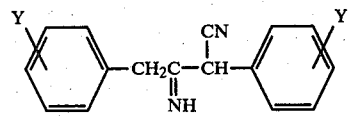

wherein Y represents a halogen atom is not substantially formed and amounts of the other by-products are also remarkably small. Thus, the object compound having high purity can be obtained in high yield.

Secondly, an aprotic polar solvent such as dimethylsulfoxide is not used. Thus, the solvent can be easily recovered. The α-isopropyl halophenylacetonitrile can be obtained by an industrial process in low cost.

Thirdly, a catalyst such as a quaternary ammonium salt is not used. Thus, it is unnecessary to have a step of recovery of a catalyst, the treatment of the discharged water can be easy to prevent an environmental pollution.

EXAMPLE 1

In a 500 ml. reactor made of stainless steel (SUS) equipped with a stirrer, 52.08 g. of solid potassium hydroxide (96% KOH), 200 ml. of xylene and 0.05 g. of polypropyleneglycol (M. W. 1,000) (0.1 wt. % to KOH) were charged and heated at 140° C. and stirred at 2000 r.p.m. for about 15 minutes and then, cooled to room temperature during the stirring.

A dispersion of fine potassium hydroxide in xylene was obtained.

According to the microscopic observation, the fine potassium hydroxide had particle sizes of 100 mµ to 10µ. No adhesion of potassium hydroxide on the inner wall of the reactor was not found.

EXAMPLE 2

In accordance with the process of Example 1 except using polyethyleneglycol (M. W. 600) instead of polypropyleneglycol, a dispersion of fine potassium hydroxide in xylene was prepared. The fine potassium hydroxide had particle sizes of 100 mµ to 10µ. No adhesion of potassium hydroxide on the inner wall of the reactor was found.

EXAMPLE 3

In accordance with the process of Example 1 except using solid sodium hydroxide instead of the solid potassium hydroxide, the dispersion of fine sodium hydroxide was prepared. The result was the same as that of Example 1.

EXAMPLE 4

In accordance with the process of Example 1 except using polyoxyethylene sorbitanmonolaurate (E. O. 20) instead of polypropyleneglycol and sitrring for 30 minutes, a dispersion of fine potassium hydroxide in xylene was prepared. The fine potassium hydroxide had particle sizes of 100 mµ to 10µ. No adhesion of potassium hydroxide on the inner wall of the reactor was found.

EXAMPLE 5

In accordance with the process of Example 4 except using solid sodium hydroxide instead of the solid potassium hydroxide, the dispersion of fine sodium hydroxide was prepared. The result was the same with that of Example 4.

EXAMPLE 6

In accordance with the process of Example 1 except using chlorobenzene, chlorotoluene, toluene, chloroform or carbon tetrachloride, instead of xylene, each dispersion of fine potassium hydroxide was prepared. The result was the same as that of Example 1.

EXAMPLE 7

In accordance with the process of Example 1 except using polyoxyethylene stearate, polyoxyethylene nonylphenyl ether, polyoxyethylene dodecyl ether, sorbitan monolaurate, fatty acid sugar ester, or glycerin monostearate instead of polypropyleneglycol, each dispersion of fine potassium hydroxide was prepared. The result was the same as that of Example 1.

These results are observed by the microscope as the microscopic photographs.

EXAMPLE 8

In a 500 ml. reactor made of stainless steel (SUS) equipped with a homomixer, 52.08 g. of solid potassium hydroxide, 200 ml. of xylene and 0.05 g. of polyoxyethylene sorbitan monolaurate (E. O. 20) were charged and heated at 140° C. (potassium hydroxide was pasty). The homomixer was rotated at 10,000 r.p.m. for 30 minutes and the dispersion was cooled to the room temperature during the stirring.

According to the microscopic observation, the fine potassium hydroxide had particle sizes of 100 mµ to 10µ. No adhesion of potassium hydroxide on the inner wall of the reactor was not found.

EXAMPLE 9

In accordance with the process of Example 8 except using solid sodium hydroxide instead of the solid potassium hydroxide, the dispersion of fine sodium hydroxide was prepared. The result was the same as that of Example 8.

REFERENCE 1

In accordance with the process of Example 1 except eliminating polypropyleneglycol, a dispersion of fine potassium hydroxide in xylene was prepared. An adhesion of potassium hydroxide on the inner wall of the reactor was found though a dispersion of fine potassium hydroxide was formed.

REFERENCE 2

In accordance with the process of Example 1 except eliminating polypropyleneglycol, and using solid sodium hydroxide instead of solid potassium hydroxide, a dispersion of fine sodium hydroxide in xylene was prepared. An adhesion of sodium hydroxide on the inner wall of the reactor was found though a dispersion of fine sodium hydroxide was formed.

REFERENCE 3

In accordance with the process of Example 1 except eliminating polypropyleneglycol, and stirring at room temperature, a dispersion of potassium hydroxide in xylene was prepared. The particles of potassium hydroxide were polygon and coarse.

EXAMPLE 10

In a 500 ml. reactor made of stainless steel (SUS) equipped with a stirrer, 52.08 g. of solid potassium hydroxide (96% KOH), 200 ml. of xylene and 0.05 g. of polypropyleneglycol (M. W. 1,000) (0.1 wt. % to KOH) were charged and heated at 140° C. and stirred at 2000 r.p.m. for about 15 minutes and then, cooled to room temperature during the stirring.

A dispersion of fine potassium hydroxide in xylene was obtained.

In the dispersion, 26 g. (0.33 mole) of isopropyl chloride was charged and then, 34 g. (0.22 mole) of 4-chlorophenylacetonitrile was added dropwise during 10 minutes at room temperature with stirring the mixture and then, the mixture was further stirred at 70° to 80° C. for 50 minutes to react them.

After the reaction, the reaction mixture was poured into 300 ml. of water. The organic layer was separated and concentrated to distil off xylene and the product was distilled under a reduced pressure to obtain 40.4 g. of α-isopropyl-4-chloro-phenylacetonitrile having a boiling point of 104°–106° C./1 mmHg (yield 95%).

REFERENCE 4

In a mortar, 50 g. (0.89 mole) of potassium hydroxide was pulverized in 200 ml. of xylene to obtain a dispersion of fine potassium hydroxide in xylene.

In accordance with the process of Example 10 except using said dispersion of fine potassium hydroxide instead of the dispersion of fine potassium hydroxide having a diameter of less than 100µ in xylene, and varying the reaction time to 8 hours, the process was repeated to obtain 29.8 g. of α-isopropyl-4-chlorophenylacetonitrile having a boiling point of 102° to 106° C./1 mmHg (yield of 70%).

EXAMPLE 11 to 15

In accordance with the the process of Example 10, the halophenylacetonitrile and isopropyl halide shown in the following table were used to obtain the corresponding α-isopropyl halophenylacetonitriles.
The results are shown in Table.

TABLE

| | Starting material | |
|---|---|---|
| | halophenylacetonitrile | isopropyl halide |
| Exp. 11 | 2-chlorophenylacetonitrile | isopropyl bromide |
| Exp. 12 | 3-chlorophenylacetonitrile | isopropyl chloride |
| Exp. 13 | 4-bromophenylacetonitrile | " |
| Exp. 14 | 3-fluorophenylacetonitrile | " |
| Exp. 15 | 4-fluorophenylacetonitrile | " |

| | Product | | |
|---|---|---|---|
| | α-isopropyl halophenyl-acetonitrile | Yield (%) | Boiling point (°C./mmHg) |
| Exp. 11 | α-isopropyl-2-chlorophenyl-acetonitrile | 90.5 | 105–106/1.1 |
| Exp. 12 | α-isopropyl-3-chlorophenyl-acetonitrile | 92 | 105–107/0.3 |
| Exp. 13 | α-isopropyl-4-bromophenyl-acetonitrile | 95 | 92–94/0.12 |
| Exp. 14 | α-isopropyl-3-fluorophenyl-acetonitrile | 91 | 87–88/4.97 |
| Exp. 15 | α-isopropyl-4-fluorophenyl-acetonitrile | 91.5 | 88–89/4.98 |

EXAMPLE 16

In accordance with the process of Example 10 except using 0.05 g. of polyoxyethylenesorbitane monolaurate as a stabilizer instead of polypropyleneglycol, the process was repeated to obtain 40 g. of α-isopropyl-4-chlorophenylacetonitrile having a boiling point of 104° to 106° C./mmHg (yield of 94%).

EXAMPLE 17 to 21

In accordance with the process of Examples 11 to 15, the halophenylacetonitrile and isopropyl halide shown in the above table were used except using polyoxyethylenesorbitane monolaurate as the stabilizer instead of polypropyleneglycol.
The results are as follows.

TABLE

| | Starting materials | Product | Yield (%) |
|---|---|---|---|
| Exp. 17 | same as Example 11 | same as Example 11 | 90 |
| Exp. 18 | same as Example 12 | same as Example 12 | 91 |
| Exp. 19 | same as Example 13 | same as Example 13 | 94 |
| Exp. 20 | same as Example 14 | same as Example 14 | 89 |
| Exp. 21 | same as Example 15 | same as Example 15 | 91 |

EXAMPLE 22

In the xylene dispersion of fine potassium hydroxide having particle diameter of less than 100μ obtained by the process of Example 1, 26 g. (0.33 mole) of isopropyl chloride was charged, and then a solution of 37.5 g. (0.22 mole) of 4-chlorophenylacetic acid in 50 ml. of xylene was added dropwise during about 10 minutes and then, the reaction was continued at 70°–80° C. for 50 minutes.

After the reaction, the reaction mixture was poured into 300 ml. of water and the organic layer was separated and concentrated to distil off xylene and the product was distilled under a reduced pressure to obtain 43 g. (yield of 91%) of α-isopropyl-4-chlorophenylacetic acid (m.p. 88°–89° C.).

EXAMPLE 23

In accordance with the process of Example 22, except using 36 g. (0.89 mole) of sodium hydroxide instead of 50 g. (0.89 mole) of potassium hydroxide and using 40.6 g. (0.33 mole) of isopropyl bromide instead of 26 g. (0.33 mole) of isorpopyl chloride, the reaction and the treatment were carried out to obtain 38.0 g. (yield of 81.2%) of α-isopropyl-4-chlorophenyl acetic acid.

EXAMPLE 24 to 44

In accordance with the process of Example 22 the active methylene compounds and the halides shown in the following table were used to obtain the corresponding product. The results are shown in Table.

TABLE

| | Starting materials | |
|---|---|---|
| | Active methylene compound | Halides |
| Exp. 24 | diethyl malonate | 1,2-dibromoethane |
| Exp. 25 | ethyl cyanoacetate | n-butyl iodide |
| Exp. 26 | methyl acetylacetate | benzyl chloride |
| Exp. 27 | 4-t-butyl phenylacetonitrile | isopropyl chloride |
| Exp. 28 | 3-trifluoromethyl phenyl-acetonitrile | isopropyl bromide |
| Exp. 29 | phenylacetonitrile | isopropyl chloride |
| Exp. 30 | α-ethylphenylacetonitrile | 1,4-dichlorobutane |
| Exp. 31 | β-cyanophenyl propionitrile | chloroacetonitrile |
| Exp. 32 | 2-methyl cyclohexanone | 3,3-dimethyl vinyl-chloride |
| Exp. 33 | 3,4-dimethoxyphenyl-acetonitrile | methyl iodide |
| Exp. 34 | 4-methoxyphenylacetic acid | isopropyl bromide |
| Exp. 35 | α-ethylphenylacetonitrile | vinyl chloride |
| Exp. 36 | 4-isopropylphenylacetonitrile | isopropyl bromide |
| Exp. 37 | 4-methoxyphenylacetonitrile | isopropyl bromide |
| Exp. 38 | 3,4-dimethylphenylacetonitrile | isopropyl chloride |
| Exp. 39 | phenylacetonitrile | ethyl iodide |
| Exp. 40 | 2,4-dichlorophenylacetonitrile | methyl iodide |
| Exp. 41 | phenylacetic acid | isopropyl bromide |
| Exp. 42 | 4-isobutylphenylacetic acid | methyl iodide |
| Exp. 43 | 3,4-dichlorophenylacetonitrile | methyl iodide |
| Exp. 44 | 2,4,6-trimethylphenylacetonitrile | ispropyl bromide |

TABLE

| | Product | Yield (%) | Melting point Boiling point |
|---|---|---|---|
| Exp. 24 | cyclopropane-1,1-dicarboxylic acid diethyl ester | 83 | m.p. 139–141° C. |
| Exp. 25 | ethyl α-n-butylcyanoacetate | 91.3 | b.p. 129–131° C./ 22 mmHg |
| Exp. 26 | methyl α-benzylacetylacetate | 92.0 | b.p. 98–109° C./ 0.05 mmHg |
| Exp. 27 | α-isopropyl-4-t-butyl phenyl-acetonitrile | 91.6 | b.p. 92–95° C./ 0.25 mmHg |
| Exp. 28 | α-isopropyl-3-trifluoromethyl-phenylacetonitrile | 92.3 | b.p. 96–97° C./ 5.1 mmHg |
| Exp. 29 | α-isopropylphenylacetonitrile | 95.0 | m.p. 50–52° C. |
| Exp. 30 | α-ethyl-α-(1-chlorobutyl) phenylacetonitrile | 73.1 | b.p. 152° C./ 1.5 mmHg |
| Exp. 31 | β-cyano-β-(cyano acetyl) phenylpropionitrile | 86.0 | m.p. 102–103° C. |
| Exp. 32 | 2-methyl-2-(3,3-dimethylvinyl)-cyclohexanone | 40.5 | b.p. 190–200° C./ |

TABLE-continued

| | Product | Yield (%) | Melting point Boiling point |
|---|---|---|---|
| Exp. 33 | α-methyl-(3,4-dimethoxyphenyl) acetonitrile | 90.2 | 40 mmHg b.p. 152–155° C. |
| Exp. 34 | α-isopropyl-4-methoxyphenylacetic acid | 85.0 | m.p. 143–145° C. |
| Exp. 35 | α-ethyl-α-vinylphenylacetonitrile | 93.5 | b.p. 116° C./7 mmHg |
| Exp. 36 | α-isopropyl-4-isopropylphenylacetonitrile | 87.1 | b.p. 100–102° C./0.4 mmHg |
| Exp. 37 | α-isopropyl-4-methoxyphenylacetonitrile | 90.4 | b.p. 95–96° C./0.15 mmHg |
| Exp. 38 | α-isopropyl-3,4-dimethylphenylacetonitrile | 87.8 | b.p. 93–95° C./0.5 mmHg |
| Exp. 39 | α-ethyl phenylacetonitrile | 91.5 | m.p. 69–70° C. |
| Exp. 40 | α-methyl-2,4-dichlorophenylacetonitrile | 92.0 | b.p. 102° C./0.9 mmHg |
| Exp. 41 | α-isopropyl phenylacetic acid | 89.5 | m.p. 62° C. |
| Exp. 42 | α-methyl-4-isobutylphenylaceticacid | 88.7 | m.p. 75–76° C. |
| Exp. 43 | α-methyl-3,4-dichlorophenylacetonitrile | 89.6 | b.p. 108° C./0.2 mmHg |
| Exp. 44 | α-isopropyl-2,4,6-trimethylphenylacetonitrile | 70.2 | b.p. 87–88° C./0.2 mmHg |

We claim:

1. In a reaction of an active methylene compound selected from the group consisting of malonic nitrile, malonic acid, diethyl malonate, cyanoacetic acid, methyl cyanoacetate, acetylacetic acid, methyl acetylacetate, acetylacetone, phenylacetonitrile, 4-ethylphenylacetonitrile, 3,4-dimethylphenylacetonitrile, 3-trifluoromethylphenylacetonitrile, phenylacetic acid, 4-chlorophenyl acetic acid, 2-bromophenyl acetic acid, 4-ethyl phenyl acetic acid, phenylthioacetonitrile, α-methylphenylacetonitrile, α-methoxyphenylacetonitrile, β-cyanophenylpropionitrile, diphenylacetonitrile, propionaldehyde, cyclohexanone and 2-methylcyclohexanone with an organoalkyl compound selected from the group consisting of alkyl halides, aralkyl halides, vinyl halides, alkyl vinyl halides, haloacetonitriles and haloacetates to produce a methylene organolkylated compound, the improvement characterized in that the reaction is carried out in an inert organic solvent dispersion of fine alkali hydroxide obtained by mixing an alkali hydroxide and an inert organic solvent, treating the mixture to form a dispersion of fine particles of the alkali hydroxide having a diameter of 100 mμ to 500μ.

2. A process according to claim 1 wherein a stabilizer is added to the inert organic solvent in the preparation of the dispersion of fine alkali hydroxide.

3. A process according to claim 2 wherein the stabilizer is a hydrophilic compound which is adsorbed on the surface of the alkali hydroxide in the inert organic solvent.

4. A process according to claim 2 wherein the stabilizer is selected from the group consisting of compounds having the formula

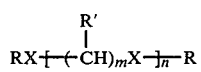

wherein R and R' are respectively hydrogen atom or $C_1$–$C_4$ alkyl group and X represents oxygen or sulfur atom; m and n are respectively 1 or more than 1; and polyoxyethylene type nonionic surfactants, fatty acid sorbitan esters, fatty acid glycerol monoesters and fatty acid sugar esters, quaternary ammonium salts, fatty amines and perfluoroalkyl surfactants is added at a ratio of more than 0.0001 wt.% to the alkali hydroxide.

5. The method of claim 1 wherein said treating comprises heating the mixture to form a paste and stirring the mixture to form a dispersion of fine particles of the alkali hydroxide, and cooling the mixture in the dispersed form while continuing stirring to yield said diameter particles.

6. A process according to claim 5 wherein the mixture is heated near the boiling point of the solvent.

7. A process according to claim 1 wherein the solvent is removed from the dispersion of the alkali hydroxide and another solvent is added to the alkali hydroxide.

8. In a reaction of a halophenylacetonitrile with an isopropyl halide to produce α-isopropyl halophenylacetonitrile, the improvement characterized in that the reaction is carried out in an inert organic solvent dispersion of fine alkali hydroxide obtained by mixing an alkali hydroxide and an inert organic solvent, heating the mixture to form a paste and stirring the mixture to form a dispersion of fine particles of the alkali hydroxide, and cooling the mixture in the dispersed form while continuing stirring to yield alkali hydroxide particles having a diameter of 100 mμ to 500μ.

* * * * *